United States Patent [19]
Inoue

[11] Patent Number: 5,871,739
[45] Date of Patent: Feb. 16, 1999

[54] PHARMACEUTICAL COMPOSITION

[75] Inventor: Eri Inoue, Himeji, Japan

[73] Assignee: Senju Pharmaceutical Co., Ltd., Osaka, Japan

[21] Appl. No.: 729,152

[22] Filed: Oct. 11, 1996

[30] Foreign Application Priority Data

Oct. 13, 1995 [JP] Japan ................................... 7-291993

[51] Int. Cl.⁶ .................................................. A61K 39/00
[52] U.S. Cl. .................. 424/185.1; 424/93.1; 424/192.1; 424/520; 514/12; 530/324
[58] Field of Search ............... 514/12–17; 530/324–330; 424/185.1, 93.1, 192.1, 520, 537, 571

[56] References Cited

FOREIGN PATENT DOCUMENTS

| 0 696 736 A1 | 2/1996 | European Pat. Off. . |
| 1499394 | 8/1989 | U.S.S.R. . |
| 08474 | 9/1989 | WIPO . |
| 89/08474 | 9/1989 | WIPO . |
| 95/03828 | 2/1995 | WIPO . |

OTHER PUBLICATIONS

Groenen et al Eur. J. Biochem. vol. 205 p. 671, 1992.
Chambers et al, J. Biol. Chem. vol. 266 p. 6742, Apr. 1991.
Hogg et al J. Biol. Chem. vol. 261 p. 12420, Sep. 1986.
I. Angunawela, "The effects of immunosuppression on the development of (experimental) cataract", Immunology, vol. 64, pp. 69–72, 1988.

*Primary Examiner*—Sheela Huff
*Attorney, Agent, or Firm*—Wenderoth, Lind & Ponack, L.L.P.

[57] ABSTRACT

A pharmaceutical composition comprising, as an active ingredient, a lens antigen which induces a lens cell damaging immune response or a microorganism capable of expressing a lens antigen which induces a lens cell damaging immune response. The pharmaceutical composition of the present invention containing, as an active ingredient, a lens antigen or a microorganism capable of expressing said antigen shows markedly superior inhibitory effects on the increase of an anti-lens protein antibody titer. Therefore, it most probably treats or prevents cataract effectively, and delays onset of cataract. Thus, the composition is extremely useful for cataract patients and reserve patients of cataract.

11 Claims, 5 Drawing Sheets

FIG. 1 (A)

untreated

FIG. 1 (B)

immunized with β_H-crystallin

PHARMACEUTICAL COMPOSITION

BACKGROUND OF THE INVENTION

1. Field of the Invention

The present invention relates to a pharmaceutical composition containing, as an active ingredient, a lens antigen or a microorganism capable of expressing said antigen. More particularly, the present invention relates to an inhibitor to the increase of antibodies against a lens protein. The present invention further relates to an agent for the therapy, prophylaxis or retardation of onset of cataract.

2. Description of Related Art

Cataract is a serious disease associated with gradual loss of eyesight caused by a lens which became opaque due to various factors. It comes out with a symptom of paropsis caused by the opacity of the lens.

Cataract has so far been treated by the administration of various pharmaceutical agents. However, administration of such agents is not entirely satisfactory, partly because the etiology of cataract has not been fully elucidated. Consequently, the treatment of cataract today ultimately relies on surgical one. The surgical treatment comprises either removal of lens nucleus and lens cortex to the outside of the membrane of the lens, or enucleation of the entire opaque lens out from the eye. However, surgical treatments often induce complications and they are burdensome to patients, since incision and suture of the cornea are inevitable even when operated with the state-of-the-art surgery technique.

To sum, the etiology of cataract has not been fully elucidated and agents for therapy thereof are not satisfactory. A surgical treatment accompanies great burden on patients.

SUMMARY OF THE INVENTION

It is therefore an object of the present invention to provide a novel pharmaceutical composition useful for the therapy of cataract and the like.

It has now been found according to the present invention that administration of a lens antigen which induces lens cell damaging immune responses (hereinafter such antigen is sometimes referred to simply as lens antigen of the present invention) leads to a suppression of the increase of anti-lens protein antibodies in sera. As shown in Experimental Examples 1 and 2 to be mentioned later, cataract is caused by lens epithelial cell damage due to autoimmunity by lens protein. Hence, the lens antigen of the present invention or a microorganism capable of expressing said antigen is useful for the therapy, prophylaxis or retardation of onset of cataract.

Thus, the present invention provides a pharmaceutical composition containing, as an active ingredient, a lens antigen capable of inducing lens cell damaging immune responses; particularly, an inhibitor of the increase of anti-lens protein antibodies. More specifically, the present invention provides a pharmaceutical composition comprising a lens antigen containing an epitope having an amino acid sequence of amino acid Nos. 2–6 depicted in Sequence Listing, SEQ ID NO:1, or amino acid Nos. 162–166 depicted in Sequence Listing, SEQ ID NO:8. Particularly, provided is a pharmaceutical composition wherein the lens antigen is a lens crystallin or a lens membrane peptide. The lens membrane peptide of the present invention includes all peptides present in or on the lens membrane, and includes peptides constituting a lens membrane protein or a receptor present in lens membrane.

The present invention further provides a pharmaceutical composition containing an animal lens homogenate as an active ingredient.

The present invention moreover provides a pharmaceutical composition containing, as an active ingredient, a microorganism capable of the expressing lens antigen which induces lens cell damaging immune responses; particularly, an inhibitor of increase of anti-lens protein antibodies, which is more particularly a pharmaceutical composition containing said active ingredient in a form suitable for intestinal administration.

The present invention still further provides the above-mentioned pharmaceutical composition for the therapy, prophylaxis or retardation of onset of cataract.

The present invention also provides a method for suppressing an increase of anti-lens protein antibodies, comprising administering an active ingredient selected from the group consisting of a lens antigen which induces a lens cell damaging immune response and a microorganism capable of expressing a lens antigen which induces a lens cell damaging immune response.

The present invention moreover provides use of an active ingredient selected from the group consisting of a lens antigen which induces a lens cell damaging immune response and a microorganism capable of expressing a lens antigen which induces a lens cell damaging immune response, for the preparation of an inhibitor of the increase of anti-lens protein antibodies.

BRIEF DESCRIPTION OF THE DRAWINGS

FIG. 1(A) and 1(B) are light microscopic photographs showing lens epithelial cells at five weeks after initial immunization of mice with $\beta_H$-crystallin.

DETAILED DESCRIPTION OF THE INVENTION

Figure 2:
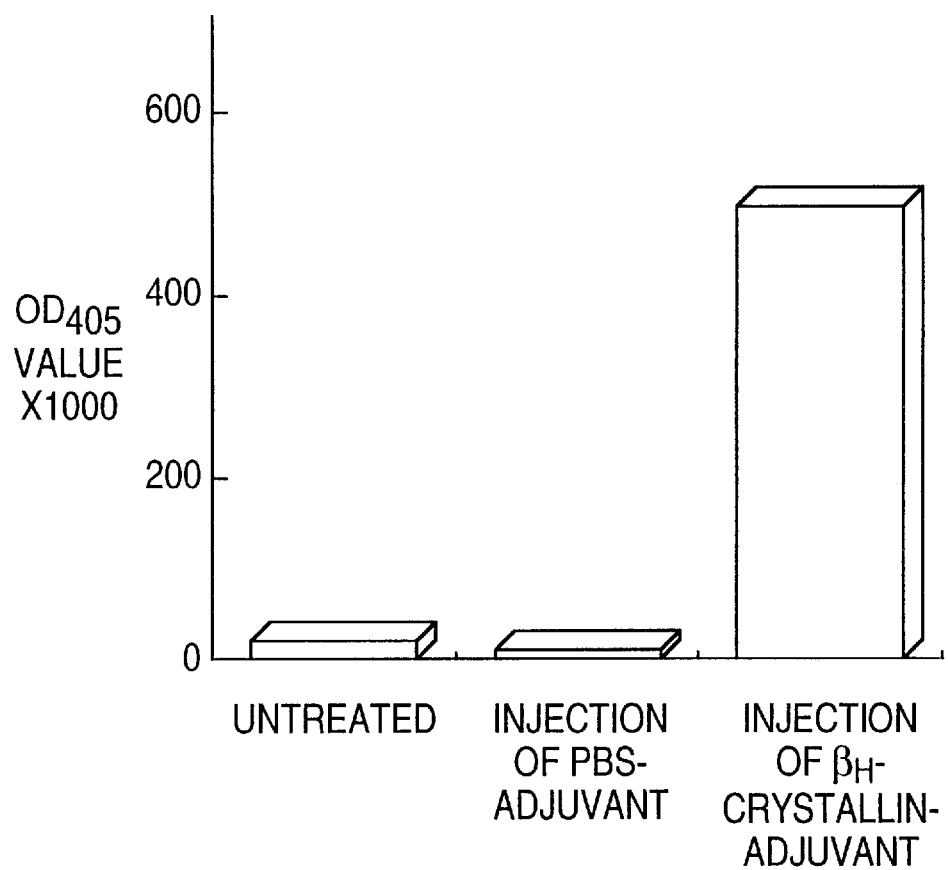
FIG. 2 is a graph showing anti-$\beta_H$-crystallin antibody titers, as determined by ELISA, of sera (diluted 10,000-fold) from mice at five weeks after initial immunization.

In the present invention, by a lens antigen is meant an antigenic substance in the lens or one having the same antigenic determinant (epitope) with that possessed by said antigenic substance. Examples thereof include proteins present in lens tissues, such as lens crystallins (e.g., α-crystallins, β-crystallins and γ-crystallins), lens membrane proteins [e.g., major intrinsic protein (MIP) and epidermal epithelial protein (EEP)] and constitutive peptide of receptor present in lens membrane. These may be naturally occurring or synthetic. A naturally occurring one may be an isolated material or a material containing the same. Such material containing an isolated material includes, for example, lens homogenate and lens epithelial cell homogenate.

The naturally occurring lens antigen is not limited in terms of derivation, and may be derived from mammals such as human, cow, horse, swine and sheep, or from a microorganism capable of expressing the lens antigen.

A lens crystallin is a typical lens antigen which induces lens cell damaging immune responses. An administration of the lens antigen of the present invention to mammals before and/or after immunization with crystallin leads to induction of immunological tolerance which enables suppression of the increase in anti-lens protein antibody titer of sera. The suppressive effects are described in detail in the following Experimental Example 7.

The epitope of the lens antigen of the present invention is not particularly limited as long as it has an amino acid sequence affording immunogenicity to produce a lens cell damaging antibody. Specific examples include amino acid sequence (amino acid Nos. 2–6) depicted in Sequence Listing, SEQ ID NO:1 and amino acid sequence (amino acid Nos. 162–166) depicted in Sequence Listing, SEQ ID NO:8. The peptides having such an amino acid sequence include human β-crystallins derived from lens, and topoisomerases of *Escherichia coli*, Salmonella and yeast, 17 kD protein of barley stripe mosaic virus, HF-1 protein of *Haemophilus influenzae* and the like derived from non-lens sources. Identification of epitope is described in detail later in Experimental Examples 3 and 4.

In the present invention, the term "microorganism" encompasses a wide range of microorganisms inclusive of viruses. Specific examples include procaryotic cells (e.g., bacteria and Actinomycetes) and fungi (e.g., filamentous fungus, yeast, Myxomycetes, Basidiomycetes and Zygomycetes), some algae, protozoa, virus and the like. These include not only wild ones but also those artificially constructed by known recombinant technology. Typical examples thereof include infectious microorganisms such as bacteria (e.g., *Neisseria meningitidis, Vibrio cholerae* and *Escherichia coli*) and viruses (e.g., Epstein-Barr virus and cytomegalovirus), since the proteins expressed thereby have the same epitope as that possessed by human crystallins.

Said microorganisms may be attenuated and used in the present invention. Attenuation can be performed by a method known Per se, such as heat and formalin treatments.

The microorganisms artificially obtained by genetic recombination include host microorganisms transformed with a recombinant vector containing a DNA encoding peptide which is a lens antigen of the present invention. The host microorganism may be, for example, bacteria such as *Escherichia coli*, genus Bacillus and lactic acid bacterium, or yeast. The recombinant vector into which said DNA is to be incorporated is not subject to any particular limitation as long as it can be replicated or self-proliferated in the above-mentioned various hosts and can express said incorporated DNA in the host. Examples thereof include plasmid DNA and phage DNA. Specific examples include pUC18, pUC19, pSP64 and the like as plasmid vectors for expression in *Escherichia coli*; pPL608, pAM α1 and the like for expression in *Bacillus subtilis*; and YEp51, pAAH5, pYE4 and the like for expression in yeast. As a phage expression vector, exemplified are λgt11, ZAPII and the like.

The pharmaceutical composition of the present invention may be, for example, an inhibitor of the increase of anti-lens protein antibodies, or an agent for therapy, prophylaxis or retardation of onset of cataract.

The lens antigen can be prepared into a preparation for administration by a conventional method generally used for formulation of a preparation. When said pharmaceutical composition is for oral administration, the preparation is desirably provided in the form suitable for absorption from digestive tract.

Examples of oral solid preparation include tablets, capsules, granules, powders and the like. These preparations may contain various components to be added according to the preparation, such as binders (e.g., syrup, gum arabic, gelatin, sorbit, tragacanth gum and polyvinylpyrrolidone); excipients (e.g., lactose, corn starch, calcium phosphate, sorbit and glycine); lubricants (e.g., magnesium stearate, talc, polyethylene glycol and silica); disintegrators (e.g., potato starch); wetting agents (e.g., sodium lauryl sulfate); dispersing agents; thickeners; flavors; emulsifiers; and the like. Tablets may be coated by a known method.

While the amount of the lens antigen to be contained in solid preparations may vary depending on the number of doses, presence or otherwise of other efficacious ingredients and so on, it is generally 0.1–500 mg/tablet.

Oral liquid preparation may be, for example, aqueous or oily suspensions, solutions, syrups or elixirs. The liquid preparations may contain additives of general use, such as suspending agents (e.g., sorbit syrup, methylcellulose, syrup, gelatin, hydroxyethylcellulose, carboxymethylcellulose and aluminum stearate gel); emulsifiers (e.g., lecitin and sorbitan monooleate); nonaqueous vehicles (e.g., almond oil, fractionated coconut oil, oily ester, propylene glycol and ethanol); preservatives; and the like.

While the amount of the lens antigen to be contained in the liquid preparations may vary depending on the number of doses, presence or otherwise of other efficacious ingredients and so on, it is generally 1 mg–100 g/100 ml.

The oral preparation may be a solid preparation to be dissolved in a suitable vehicle, such as water, when in use.

When the pharmaceutical composition is an intravenous preparation, pH adjusting agents, buffers, stabilizers, preservatives, solubilizers and the like may be added to the lens antigen as necessary, and the mixture is prepared into an intravenous preparation by a conventional method.

The lens antigen of the present invention is administered orally (inclusive of intestinal administration, intragastric administration and inhalation) or parenterally (e.g., intravenous administration). While the dose thereof may vary depending on titers of anti-lens protein antibodies in sera, degree of progression of cataract, severity of the disease, tolerance to drugs and the like, it is generally 0.1 mg–10 g, preferably 1 mg–1 g, more preferably 10 mg–100 mg in an antigen amount daily for an adult by oral administration, which may be administered in a single dose or several doses. The preparation may be prepared in a most suitable form according to the administration route.

Inasmuch as the lens antigen is a biological component, it is low toxic and causes less side-effects.

When the lens antigen of the present invention is derived from a microorganism, the microorganism itself may be administered. Particularly, it may be administered in the form of an intestinal preparation and administered particularly into small intestine.

Said microorganism can be provided as an oral preparation suitable for maintaining viable counts in the preparation and for easy absorption from intestine, which is in the form of a solid preparation or liquid preparation. A method for maintaining viable counts in the preparation, namely, a method for stabilization of the microorganism includes, for example, dispersion of microorganism in anhydrous media, addition of stabilizers to the preparation, coating of microorganism, and the like, which is selected as appropriate according to the form of the preparation.

Examples of the solid preparation include granules, powders, tablets, capsules and the like. Such preparations may contain suitable components depending on the preparation, such as binders (e.g., polyvinylpyrrolidone, hydroxypropylcellulose, sucrose fatty acid ester, gum arabic, gelatin and pullulan); excipients (e.g., lactose and corn starch); lubricants (e.g., magnesium stearate, talc, polyethylene glycol and silica); disintegrators (e.g., potato starch); wetting agents (e.g., sodium lauryl sulfate); adjuvants; and the like.

To make the preparation enteric-coated and to stabilize the microorganism, for example, the following coating may be preferably applied to the solid preparation.

The coating agent may be a liposoluble substance known per se, such as synthetic and semisynthetic substances (e.g., carboxymethyl-cellulose, hydroxymethylcellulose phthalate and Eudragit); natural substances such as shellac; admixture of copolymer of methacrylic acid and ethyl acrylate, and copolymer of methacrylic acid and methyl methacrylate; and the like.

A stabilizer may be contained to stabilize the microorganism. Examples of the stabilizer include polyvinylpyrrolidone, sodium carboxymethylcellulose, sodium polyacrylate, sodium arginate and the like.

While the amount of the microorganism in the solid preparation may vary depending on the number of doses, the presence or otherwise of other efficacious ingredients and the like, the viable count is generally $10^3$–$10^{10}$ cells/tablet.

Examples of oral liquid preparation include aqueous or oily suspensions, solutions, syrups, pastes, gels, elixirs and the like. Such liquid preparation can be produced by a method including addition of suspending agents such as arginic acid or sodium salt thereof, processed starches such as dextrin, pectin, carrageenan, locust bean gum, guar gum, cod gum, xanthane gum, gelatin and the like to water or a solution containing a microorganism, a method including dispersing, in a solution, a complex of microorganism and lipid in the form of a liposome, emulsion or micelle, and the like. It is also preferable that the microorganism be stabilized in a liquid preparation, and particularly preferred is the microorganism uniformly dispersed in the preparation.

Said liquid preparation may contain conventional additives, such as suspending agents, emulsifiers, nonaqueous vehicles, preservatives, adjuvants, and the like.

While the amount of the microorganism in the liquid preparation may vary depending on the number of doses, the presence or otherwise of other efficacious ingredients and the like, its viable count is generally $1\times10^3$–$5\times10^{10}$ cells/100 ml.

The oral preparation may be a solid preparation to be dissolved in a suitable vehicle, such as water, when in use.

While the dose of the microorganism capable of expressing the lens antigen of the present invention may vary depending on titers of anti-lens protein antibodies in sera, degree of progression of cataract, severity of the disease, tolerance to drugs, as well as expression efficiency of said antigen and the like, it is generally 1 mg–100 g, preferably 10 mg–10 g, more preferably 100 mg–1 g in a raw material weight of the microorganism daily for an adult, which may be administered in a single dose or plural doses. The preparation may be prepared into a most suitable form according to the administration route.

The possibility that the lens antigen of the present invention and microorganism capable of expressing the lens antigen of the present invention may have effects of therapy, prophylaxis or retardation of onset of cataract is strongly suggested from Experimental Examples 2 and 7 to be described later.

The present invention is further explained in detail by way of Examples in the following, and the effects of the present invention are clarified by Experimental Examples. These are mere examples which in no way limit the scope of the present invention.

EXPERIMENTAL EXAMPLE 1

Induction of lens epithelial cell damage by immunization with lens homogenate or crystallin Lewis rats (female, a year old) were divided into two groups (each containing four rats), and immunized five times with an emulsion of lens homogenate (first group) or β-crystallin (second group), and complete Freund adjuvant (CFA). As a result, severe lens epithelial cell damage was observed in all animals of the first and the second groups at 21 days after the first immunization. The ocular tissues of the rats of the control group, which were given an injection of a phosphate buffered saline (PBS)-CFA emulsion, were the same as those of untreated rats. From the above results, it was found that lens constituent components, preferably crystallins, particularly β-crystallin, were effective immunogens which induced lens epithelial cell damage.

EXPERIMENTAL EXAMPLE 2

Increase of sera antibodies against crystallins and induction of lens epithelial cell damage by immunization with β-crystallin The antigen was narrowed down to a single $β_H$-crystallin, and mice were immunized therewith.

Purified β_H-crystallin (manufactured by Sigma) was dissolved in PBS, prepared into an emulsion with CFA at a ratio of 1:1, and adjusted to a final concentration of 1 mg/ml. Mice (C57BL, female, 6 months old) were immunized with said emulsion (100 μl/animal). After the first immunization, four booster injections were given every other week. For boosters, the same procedure as above was followed except incomplete Freund adjuvant (IFA) was used instead of CFA. At 5 weeks after the first immunization, blood was taken from the mice. The mice were euthanized, and eyeballs were removed for histopathological examinations.

Experiment 1

Figures 1A, 1B:
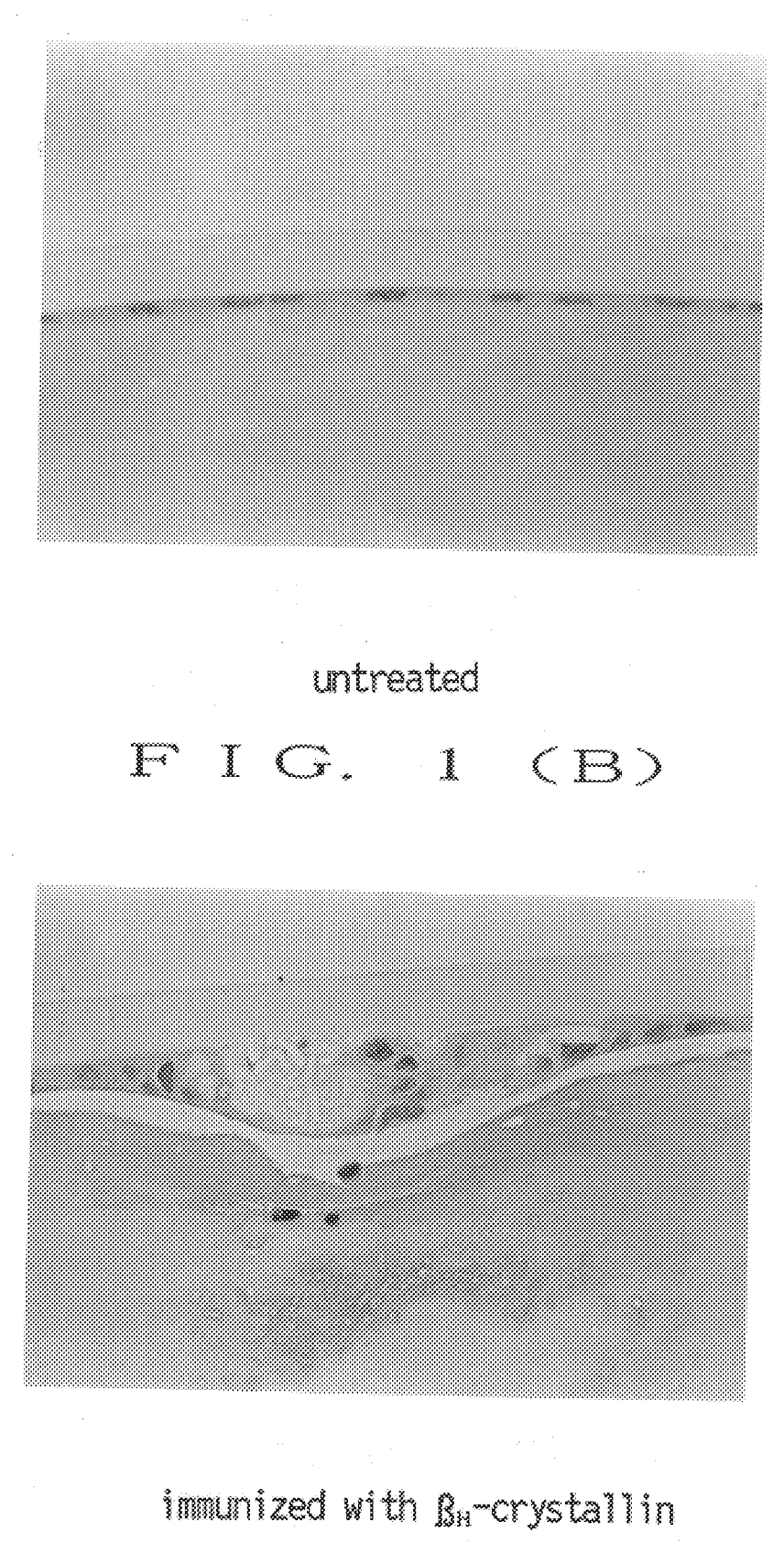

Light microscopic sections of the removed eyeballs were prepared and subjected to evaluation of lens epithelial cells. As a result, lens epithelial cell damage was found in the ocular tissues of immunized mice (FIG. 1).

Experiment 2

The antibody titer against β_H-crystallin in the collected sera was determined by enzyme-linked immunosorbent assay (ELISA). The antigen of β_H-crystallin was immobilized on 96-well microtiter plates at a concentration of 10 μg/ml. After blocking, the sera of the immunized mice were diluted to $10^3$–$10^6$-fold and reacted with the antigen. After washing, alkaline phosphatase-conjugated goat anti-mouse IgG was reacted as a secondary antibody. After washing, antibody titer was determined by color development of substrate solution of paranitrophenylphosphoric acid (pNPP). As a result, the antibody titer against β_H-crystallin in the sera of the immunized mice was extremely higher than that of untreated mice and mice immunized with PBS-adjuvant emulsion (FIG. 2).

From the above results, it was found that lens epithelial cell damage appeared with increasing titers of antibodies against β_H-crystallins. In other words, these results clearly suggest that the lens epithelial cell damage due to autoimmunity are concerned with the pathogenesis of cataract.

EXPERIMENTAL EXAMPLE 3

Identification of epitope of human βA_3-crystallin

Experiment 1

Fifteen kinds of oligopeptides (19 amino acid residues; sequence shown in Table 1) constituting human βA_3-crystallins having a known amino acid sequence were synthesized by a conventional method, and subjected to competitive inhibition assay of βA_3-crystallins and respective oligopeptides.

As the antigen, β-crystallin (containing about 10% βA_3-crystallin) was immobilized on microtiter plates at a concentration of 10 μg/ml. After blotting, β-crystallin monoclonal antibody (1 μg/ml and respective oligopeptides were added and the mixture was reacted with antigen. After washing, alkaline phosphatase-conjugated goat anti-mouse IgG was reacted as a secondary antibody. After washing, competitive inhibitory activity of peptide against the antigen was determined by color development of substrate pNPP. As a result, peptide No. 1 showed a strong binding inhibitory effect on βA_3-crystallin. This suggests that the binding site (epitope) of βA_3-crystallin to the antibody was present in N terminal 19 amino acid residues (peptide No. 1).

TABLE 1

Inhibitory effect on BA_3-crystallin-antibody binding by human BA_3-crystallin partial peptides (1)

| peptide No. | amino acid sequence[1] | site[2] | binding inhibition[3] |
|---|---|---|---|
| 1 | METQAEQQELETLPTTKMA SEQ ID NO. 13 | 1–19 | +++ |
| 2 | TTKMAQTNPTPGSLGPWKI SEQ ID NO. 14 | 15–33 | − |
| 3 | GPWKITIYDQENFQGKRME SEQ ID NO. 15 | 29–47 | − |
| 4 | GKRMEFTSSCPNVSERSFD SEQ ID NO. 16 | 43–61 | − |
| 5 | ERSFDNVRSLKVESGAWIG SEQ ID NO. 17 | 57–75 | − |
| 6 | GAWIGYEHTSFCGQQFILE SEQ ID NO. 18 | 71–89 | − |
| 7 | QFILERGEYPRWDAWSGSN SEQ ID NO. 19 | 85–103 | − |
| 8 | WSGSNAYHMERLMSFRPFG SEQ ID NO. 20 | 99–117 | − |
| 9 | FRPFGSANHKESKMTIFEK SEQ ID NO. 21 | 113–131 | − |
| 10 | TIFEKENFIGRQWEISDDY SEQ ID NO. 22 | 127–145 | − |
| 11 | ISDDYPSLQAMGWFNNEVG SEQ ID NO. 23 | 141–159 | − |
| 12 | NNEVGSMKIQSGAWVGYHY SEQ ID NO. 24 | 155–173 | − |
| 13 | VCYHYLGYRGYQYILKCDH SEQ ID NO. 25 | 169–187 | − |
| 14 | LKCDHHEGDYKHWREWGSH SEQ ID NO. 26 | 183–201 | − |
| 15 | EWGSHAQTSQIQSIRRIQQ SEQ ID NO. 27 | 197–215 | − |

[1]Amino acids are expressed by one letter symbols according to recommendation of IUPAC-IUB Commission on Biochemical Nomenclature.
[2]The amino acid number of Sequence Listing SEQ ID NO: 1.
[3]+++: inhibited binding by 50% at less than 250 μg of peptide
++: inhibited binding by 50% at not less than 250 μg and less than 500 μg of peptide
+: inhibited binding by 50% at not less than 500 μg and less than 750 μg of peptide
−: no binding inhibitory effect Experiment 2

The N terminal region (peptide No. 1) of βA_3-crystallin was cut into smaller units of 6 or 7 residues to synthesize three kinds of peptides (peptide Nos. 16, 17 and 18), which were subjected to competitive inhibition assay with βA_3-crystallin in the same manner as in Experiment 1. As a result, only peptide No. 16 had βA_3-crystallin binding inhibitory effect (Table 2). From these results, the presence of epitope in peptide No. 16 (sequence : METQAE) was suggested.

TABLE 2

Inhibitory effect on BA₃-crystallin-antibody binding by
human BA₃-crystallin partial peptides (2)

| peptide No. | amino acid sequence[1] | site[2] | binding inhibition[3] |
|---|---|---|---|
| 1 | METQAEQQELETLPTTKMA SEQ ID NO. 13 | 1–19 | +++ |
| 16 | METQAE SEQ ID NO. 28 | 1–6 | ++ |
| 17 | QQELET SEQ ID NO. 29 | 7–12 | − |
| 18 | LPTTKMA SEQ ID NO. 30 | 13–19 | − |

[1]Amino acids are expressed by one letter symbols according to recommendation of IUPAC-IUB Commission on Biochemical Nomenclature.
[2]The amino acid number of Sequence Listing SEQ ID NO: 1.
[3]+++: inhibited binding by 50% at less than 250 μg of peptide
++: inhibited binding by 50% at not less than 250 μg and less than 500 μg of peptide
+: inhibited binding by 50% at not less than 500 μg and less than 750 μg of peptide
−: no binding inhibitory effect Experiment 3

To identify the minimum unit of βA₃-crystallin epitope, one residue of six amino acid residues of peptide No. 16 was substituted by isoleucine residue to give six kinds of analogs (peptide Nos. 19–24) of peptide No. 16. In the same manner as in Experiment 1, competitive inhibition assay of βA₃-crystallins and these peptides was performed. As a result, five kinds of peptide No. 16 analogs except peptide No. 19 showed lower inhibitory activity on binding of βA₃-crystallin to antibody as compared to peptide No. 16. Peptide No. 19 alone strongly inhibited binding of βA₃-crystallin to antibody like peptide No. 16 (Table 3). These results suggest that the five consecutive amino acid residues (sequence: ETQAE) of peptide No. 16 except the first methionine was the epitope of βA₃-crystallin.

TABLE 3

Inhibitory effect on BA₃-crystallin-antibody binding by
human BA₃-crystallin partial peptides analogs

| peptide No. | amino acid sequence[1, 2] | binding inhibition[3] |
|---|---|---|
| 16 | METQAE (28) | ++ |
| 19 | IETQAE (2) | ++ |
| 20 | MITQAE (3) | + |
| 21 | MEIQAE (4) | + |
| 22 | METIAE (5) | + |
| 23 | METQIE (6) | + |
| 24 | METQAI (7) | − |
| PBS (control) | − | |

TABLE 3-continued

Inhibitory effect on BA₃-crystallin-antibody binding by
human BA₃-crystallin partial peptides analogs

| peptide No. | amino acid sequence[1, 2] | binding inhibition[3] |
|---|---|---|

[1]Amino acids are expressed by one letter symbols according to recommendation of IUPAC-IUB Commission on Biochemical Nomenclature.
[2]The numerals in parentheses show Sequence Listing SEQ ID Numbers wherein said sequences are depicted.
[3]+++: inhibited binding by 50% at less than 250 μg of peptide
++: inhibited binding by 50% at not less than 250 μg and less than 500 μg of peptide
+: inhibited binding by 50% at not less than 500 μg and less than 750 μg of peptide
−: no binding inhibitory effect Experimental Example 4

Identification of human βB₂-crystallin epitope

Seventeen kinds of oligopeptides (17 amino acid residues; sequence shown in Table 4) constituting human βB₂-crystallins having a known amino acid sequence were synthesized by a conventional method, and subjected to competitive inhibition assay of βB₂-crystallins and respective oligopeptides in the same manner as in Experiment 1 of Experimental Example 3. As a result, peptide No. 38 had strong inhibitory effect on binding of βB₂-crystallin. This suggests that the binding site (epitope) of βB₂-crystallin to the antibody was present in 17 amino acid residues of peptide No. 38.

TABLE 4

Inhibitory effect on BB₂-crystallin-antibody binding by
human BB₂-crystallin partial peptides

| peptide No. | amino acid sequence[1] | site[2] | binding inhibition[3] |
|---|---|---|---|
| 25 | MASDHQTQAGKPQSLNP SEQ ID NO. 31 | 1–17 | − |
| 26 | QSLNPKIIIFEQENPQG SEQ ID NO. 32 | 13–29 | − |
| 27 | ENFQGHSHELNGPCPNL SEQ ID NO. 33 | 25–41 | − |
| 28 | PCPNLKETGVEKAGSVL SEQ ID NO. 34 | 37–53 | − |
| 29 | AGSVLVQAGPWVGYEQA SEQ ID NO. 35 | 49–65 | − |
| 30 | GYEQANCKGEQFVFEKG SEQ ID NO. 36 | 61–77 | − |
| 31 | VFEKGEYPRWDSWTSSR SEQ ID NO. 37 | 73–89 | − |
| 32 | WTSSRRTDSLSSLRPIK SEQ ID NO. 38 | 85–101 | − |
| 33 | LRPIKVDSQEHKIILYE SEQ ID NO. 39 | 97–113 | − |
| 34 | IILYENPNFTGKKMEII SEQ ID NO. 40 | 109–125 | − |
| 35 | KMEIIDDDVPSFHAHGY SEQ ID NO. 41 | 121–137 | − |
| 36 | HAHGYQEKVSSVRVQSG SEQ ID NO. 42 | 133–149 | − |

TABLE 4-continued

Inhibitory effect on BB$_2$-crystallin-antibody binding by human BB$_2$-crystallin partial peptides

| peptide No. | amino acid sequence[1] | site[2] | binding inhibition[3] |
|---|---|---|---|
| 37 | RVQSGTWVGYQYPGYRG SEQ ID NO. 43 | 145–161 | – |
| 38 | PGYRGLQYLLEKGDYKD SEQ ID NO. 44 | 157–173 | +++ |
| 39 | GDYKDSSDFGAPHPQVQ SEQ ID NO. 45 | 169–185 | – |
| 40 | HPQVQSVRRIRDMQWHQ SEQ ID NO. 46 | 181–197 | – |
| 41 | RIRDMQWHQRGAFHPSN SEQ ID NO. 47 | 189–205 | – |

[1]Amino acids are expressed by one letter symbols according to recommendation of IUPAC-IUB Commission on Biochemical Nomenclature.
[2]The amino acid number of Sequence Listing SEQ ID NO: 1.
[3]+++: inhibited binding by 50% at less than 250 µg of peptide
++: inhibited binding by 50% at not less than 250 µg and less than 500 µg of peptide
+: inhibited binding by 50% at not less than 500 µg and less than 750 µg of peptide
–: no binding inhibitory effect A peptide obtained by dividing peptide No. 38 having a partial sequence of βB$_2$-crystallin was synthesized and the epitope region was further narrowed down by the same method as used in Experiment 2 of Experimental Example 3. Further, the minimum unit of βB$_2$-crystallin epitope was identified in the same manner as in Experiment 3 of Experimental Example 3. As a result, the epitope was found to be consecutive five amino acid residues of amino acid Nos. 162–166 (sequence : LQYLL) in the amino acid sequence (SEQ ID No:8) of βB$_2$-crystallin.

Experimental Example 5

Induction of lens epithelial cell damage and cross reaction by non-lens derivation peptides having the same epitope with human βA$_3$-crystallin A non-lens derivation peptide having the same epitope with that of βA$_3$-crystallin, namely, the peptide having an amino acid sequence of ETQAE, was searched using a Gene Bank database. As a result, proteins of microorganisms such as *Escherichia coli*, Salmonella, yeast and virus were found to have the said amino acid sequence (Table 5).

In addition, sequence homology of non-lens derivation peptides and human crystallin other than said epitope sequence was searched to confirm homologous sequences of peptides derived from the three kinds of animals shown in Table 6 and crystallin.

TABLE 5

Non-lens derivation proteins having the same epitope with that of human BA$_3$-crystallin

| microorganism | protein |
|---|---|
| *Escherichia coli* | topoisomerase[1] |
| yeast | topoisomerase |
| Salmonella | topoisomerase |
| barley stripe mosaic virus (BSMV) | 17 kD protein |
| *Haemophilus influenzae* | HF-1 protein |

[1]Topoisomerase of *Escherichia coli* contained amino acid sequence (GLTETQAEAILE, Sequence Listing, SEQ ID NO: 9) of peptide I used in this Experimental Example.

TABLE 6

Non-lens derivation peptides having sequence homology with human crystallin besides epitope sequence of human BA$_3$-crystallin

| organism | partial amino acid sequence of peptides containing homologous sequence with crystallin[1], [2], [3] |
|---|---|
| coxsackievirus | MQYHYLGRTGYT (10) |
| nematode (*C. elegans*) | DFATIFEKNAFL (11) [peptide II] |
| baboon endogenous virus | QKLGPWKRPVAY (12) [peptide III] |

[1]Amino acids are expressed by one letter symbols according to recommendation of IUPAC-IUB Commission on Biochemical Nomenclature.
[2]The underlined sequences are homologous with human BA$_3$-crystallin.
[3]Numerals in parentheses show Sequence Listing SEQ ID Numbers wherein said sequences are depicted.

Mice were immunized with either the topoisomerase partial amino acid sequence (peptide I) of *Escherichia coli* listed in Table 5 or the two kinds of peptides (peptides II, III) shown in Table 6, and antibody titer was measured.

Mice (B6C3, female, a year old) were divided into four groups (each containing two mice) and immunized with 100 µg/animal of one of peptides I-III. After the first immunization, booster injections (100 µg/animal of each peptide) were given twice every two weeks. In the same manner as in Experimental Example 2, an emulsion of the antigen and adjuvant was prepared and used for immunization. At 5 weeks after the first immunization, blood was taken from the mice. The mice were euthanized, and eyeballs were removed. In the same manner as in Experimental Example 2, antibody titer was determined by ELISA, and light microscopic sections of ocular tissues were prepared and subjected to evaluation of lens epithelial cells.

As a result, all mice immunized with peptide I (inclusive of βA$_3$-crystallin epitope) showed mild lens epithelial cell damage. The sera taken from the mice immunized with peptide I showed cross reactivity with β-crystallin (Table 7). The other two kinds of peptides did not induce lens epithelial cell damage, nor did they show cross reactivity with β-crystallin.

TABLE 7

Expression of lens epithelial cell damage in mice immunized with peptides containing crystallin homologous sequence, and anti-crystallin antibody titer of sera

| antigen | antibody titer[1] | frequency of lens epithelial cell damage (%) |
| --- | --- | --- |
| peptide I | 1/10,000 | 100 |
| peptide II | 1/500 | 0 |
| peptide III | 1/500 | 0 |
| PBS (control) | 1/500 | 0 |

[1] The antibody titer is expressed as dilution ratio of sections when absorbance at 405 nm doubled blank values.

Experimental Example 6

Recombinant *Escherichia coli* capable of expressing β-crystallin which induces lens epithelial cell damage Rat βB$_2$-crystallin cDNA (Aaits, H. J. et al., Eur. J. Biochem., 183: 31–36, 1989) was subcloned into a commercially available expression vector pKK223-3 (manufactured by Pharmacia Biotech), and *Escherichia coli* JM105 (manufactured by Pharmacia Biotech) was transformed with said recombinant vector to express βB$_2$-crystallin in the host *Escherichia coli*. Said transformed cells were incubated in an LB medium containing 30 μg/ml of ampicillin at 37° C. for 24 hr. Using *Escherichia coli* JM105 transformed with pKK223-3 as a control, the following experiment was performed.

Mice (B6C3, female, a year old) were divided into two groups (each containing four mice) and immunized with recombinant *Escherichia coli* β-B$_2$-pKK (1,000 μg/0.2 ml) which expresses βB$_2$-crystallin. After the first immunization, booster injections (1,000 μg/animal) were given twice every two weeks. The lenses were examined with a slit lamp every two weeks. At 7 weeks after the first immunization, blood was taken from the mice and cross reactivity was determined by ELISA in the same manner as in Experimental Example 2.

The polypeptide sequences of β-crystallin of mouse and rat were extremely similar, and βA$_3$-crystallin and βB$_2$-crystallin showed high homology of 90% or more including the epitope moiety.

All mice immunized with *Escherichia coli* β-B$_2$-pKK which expressed βB$_2$-crystallin showed lens epithelial cell damage at 7 weeks after the first immunization. The lymphonodus cells of mice immunized with *Escherichia coli* which expressed βB$_2$-crystallin showed cross reactivity with β-crystallin (Table 8). Moreover, the sera antibodies against βB$_2$-crystallin showed increase in these mice. In contrast, the mice immunized with control *Escherichia coli* JM105 (incapable of expressing βB$_2$-crystallin) showed no cross reactivity of lyphocytes or an increase in antibody titer of the sera. The lenses of the mice of the control group did not display abnormality. From the foregoing results, it was evident that autoantigen expressed by *Escherichia coil* destroyed immunological tolerance and induced lens epithelial cell damage.

TABLE 8

Expression of lens epithelial cell damage in mice immunized with recombinant *Escherichia coli* which expressed B-crystallin, and anti-crystallin antibody titer of sera

| antigen | antibody titer[1] | frequency of lens epithelial cell damage (%) |
| --- | --- | --- |
| *Escherichia coli* (B-B$_2$-pKK) capable of expressing BB$_2$-crystallin | 1/2,000 | 100 |
| *Escherichia coli* (JM105) incapable of expressing BB$_2$-crystallin | 1/500 | 0 |

[1] The antibody titer is expressed as dilution ratio of sections when absorbance at 405 nm doubled blank values.

Experimental Example 7

Suppression of increase of anti-β-crystallin antibodies in sera from mice immunized by oral administration of lens homogenate Experiment 1

Male and female C57BL mice (15–16 months old) were divided into a lens group and a BSA group, and immunized with bovine β-crystallin. Bovine lens was homogenized with phosphate buffered saline (PBS) to the protein amount of 20 mg/ml and orally administered to the lens group at 0.2 ml/animal (4 mg/animal) once every four days from 26 days before the first immunization to the day of the first immunization. As a control protein, bovine serum albumin (BSA) was dissolved in PBS to 20 mg/ml and orally administered to the BSA group in the same manner as in the lens group.

Experiment 2

Male and female C57BL mice (15–16 months old) were divided into a PBS group, a lens group and a BSA group, and immunized with bovine β-crystallin. In the same manner as in Experiment 1, the lens group and BSA group underwent oral administration once every four days from 26 days before the first immunization to 34 days after the first immunization. PBS (0.2 ml/animal) was orally administered to the PBS group.

Experiment 3

Male and female C57BL mice (15–16 months old) were divided into a lens group and a BSA group, and immunized with bovine β-crystallin. In the same manner as in Experiment 1, the lens group and BSA group underwent oral administration once every four days from the day of the first immunization to 34 days after the first immunization.

β-Crystallin was isolated from bovine lens and prepared into an emulsion with CFA at a ratio of 1:1. The β-crystallin (1 mg/ml) was administered subcutaneously from the tail of the mice of Experiments 1–3 by 0.1 ml/animal (0.1 mg/animal) for immunization. After the first immunization, booster injections were given twice every two weeks. For boosters, the same procedure as above was followed except that IFA was used instead of CFA. At every other week after the first immunization, blood was taken from the mice and antibody titer of sera against β-crystallin was determined by ELISA in the same manner as in Experimental Example 2.

Figure 3:
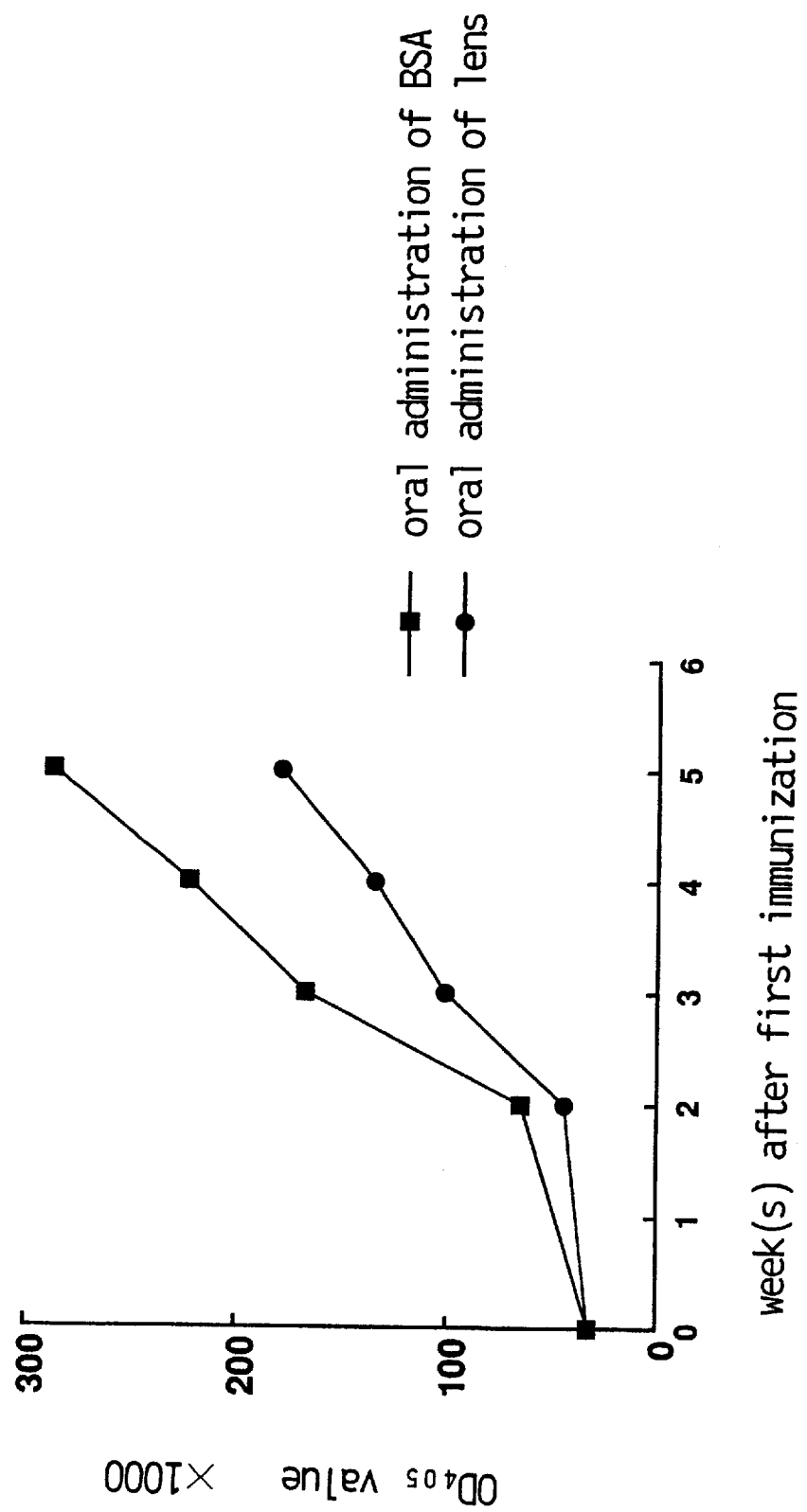
FIG. 3 is a graph showing titers of anti-$\beta$-crystallin antibodies in sera (diluted 10,000-fold) from mice at two, three, four or five weeks after the first immunization, as determined by ELISA with regard to mice orally administered with a lens homogenate from 26 days before immunization to the day of the first immunization.
Figure 4:
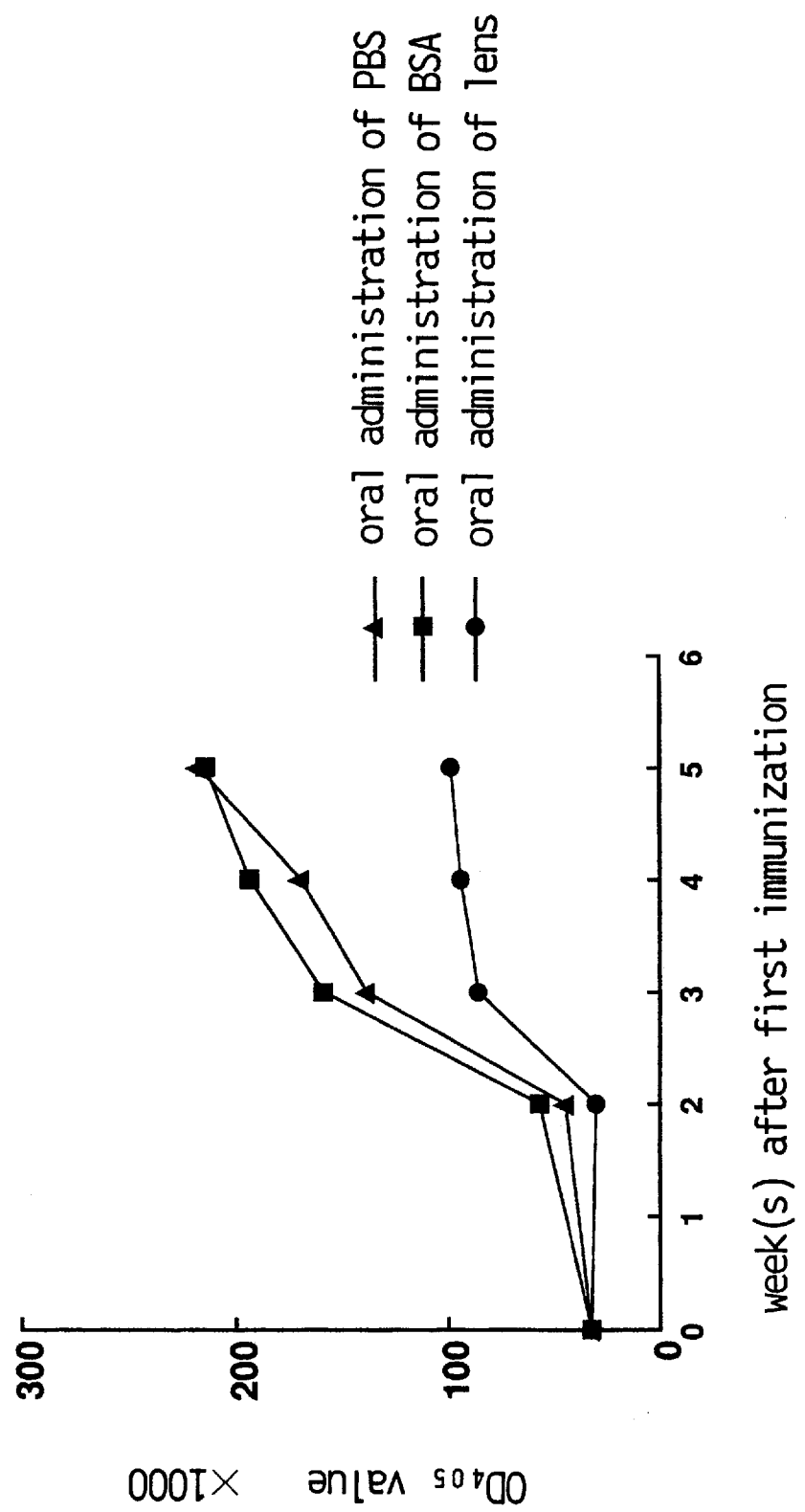
FIG. 4 is a graph showing titers of anti-$\beta$-crystallin antibodies in sera (diluted 10,000-fold) from mice at two, three, four or five weeks after the first immunization, as determined by ELISA with regard to mice orally administered with a lens homogenate from 26 days before immunization to 34 days after the first immunization.
Figure 5:
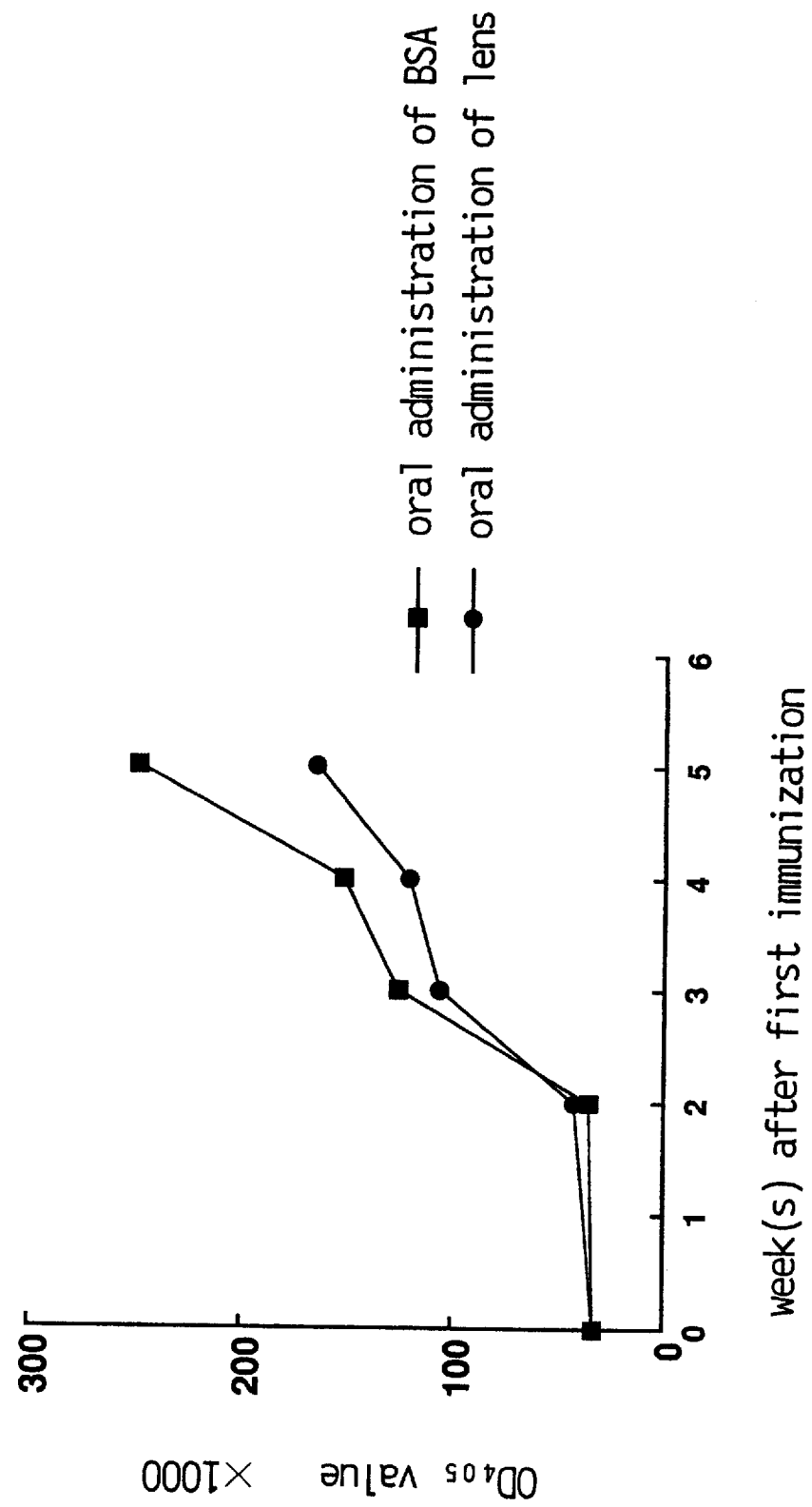
FIG. 5 is a graph showing titers of anti-$\beta$-crystallin antibodies in sera (diluted 10,000-fold) from mice at two, three, four or five weeks after the first immunization, as determined by ELISA with regard to mice orally administered with a lens homogenate from the day of the first immunization to 34 days from the first immunization.

With respect to each experiment, antibody titers of sera against antigens (β-crystallins) at 3, 4 and 5 weeks after the first immunization are shown in FIGS. 3–5. The antibody titers of the sera from C57BL mice immunized with β-crystallin elevated at 3 and 4 weeks after the first immunization in Experiments 1–3, with the highest peak present at 5 weeks after the first immunization. In Experiment 2, mice underwent oral administration before and after the first immunization. The antibody titers of the lens group administered with lens homogenate showed noticeably lower values than the BSA group (control) at 4 and 5 weeks after the first immunization (FIG. 4). In Experiment 1, mice underwent oral administration before the first immunization, and in Experiment 3, mice underwent oral administration after the first immunization. The antibody titers of the lens group mostly stayed lower than those of BSA group (FIGS. 3 and 5).

From the above results, it was clarified that administration of lens homogenate before and/or after immunization with β-crystallin suppressed increase in antibody titer of sera against antigen. It is preferable to start administration of the preparation of the present invention prior to immunization, and continue administration even after immunization, so that an increase in the antibody titers can be significantly suppressed.

| Formulation Example 1 | |
|---|---|
| [Formulation of tablets] | |
| Recombinant yeast (Sasccharomyces cerevisiae)[1] | 80% |

| -continued | |
|---|---|
| Formulation Example 1 | |
| Crystalline cellulose | 1% |
| Lactose | 10% |
| Corn starch | 5% |
| Anhydrous calcium phosphate | 2% |
| Hydroxypropylcellulose | 1% |
| Magnesium stearate | 1% |
| Total | 100% |

[1]Prepared by transformation of yeast to enable expression of crystallin, using a commercially available yeast transformation kit (Yeast Starter Kit, Bio-Rad).

Tablets were prepared by a conventional method according to the above-mentioned formulation, and applied with an enteric coating by a conventional method to give enteric-coated tablets.

The pharmaceutical composition of the present invention containing, as an active ingredient, a lens antigen or a microorganism capable of expressing said antigen shows marked inhibitory effects on the increase of an anti-lens protein antibody titer. Therefore, it most probably treats or prevents cataract effectively, and delays onset of cataract. Thus, the composition is extremely useful for cataract patients and reserve patients of cataract.

What is claimed is:

1. A suppressant of lens cell-damaging immune response, comprising a microorganism transformed with an expression vector having a DNA encoding β-crystallin and a pharmaceutically acceptable carrier.

2. The suppressant claim 1, which is in the form of a preparation for oral administration.

3. The suppressant of claim 2, which is in the form of a preparation for intestinal absorption.

4. The suppressant of claims 1, 2 or 3, which is an agent for the therapy, prophylaxis or retardation of onset of cataract.

5. A method for suppressing lens cell-damaging immune response in a mammal, comprising orally administering an effective amount of a β-crystallin to said mammal.

6. A method for suppressing lens cell-damaging immune response in a mammal, comprising orally administering, to said mammal, an effective amount of a microorganism transformed with an expression vector having a DNA encoding β-crystallin.

7. The method of claim 5 or 6, wherein said β-crystallin microorganism is in the form of a preparation for intestinal absorption.

8. The method of claim 5 or 6, which is for the therapy, prophylaxis or retardation of onset of cataract.

9. A method for suppressing lens cell-damaging immune response in a mammal, comprising orally administering an effective amount of a lens homogenate to said mammal.

10. The method of claim 9, wherein said homogenate is in the form of a preparation for intestinal absorption.

11. The method of claim 9, which is for the therapy, prophylaxis or retardation of onset of cataract.

* * * * *

SEQUENCE LISTING ( 1 ) GENERAL INFORMATION:

( i i i ) NUMBER OF SEQUENCES: 47

( 2 ) INFORMATION FOR SEQ ID NO: 1:

( i ) SEQUENCE CHARACTERISTICS:
        ( A ) LENGTH: 215 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: protein ( x i ) SEQUENCE DESCRIPTION: SEQ ID NO: 1:

```
Met Glu Thr Gln Ala Glu Gln Gln Glu Leu Glu Thr Leu Pro Thr Thr
 1               5                  10                  15

Lys Met Ala Gln Thr Asn Pro Thr Pro Gly Ser Leu Gly Pro Trp Lys
            20                  25                  30

Ile Thr Ile Tyr Asp Gln Glu Asn Phe Gln Gly lys Arg Met Glu Phe
        35                  40                  45

Thr Ser Ser Cys Pro Asn Val Ser Glu Arg Ser Phe Asp Asn Val Arg
    50                  55                  60

Ser Leu Lys Val Glu Ser Gly Ala Trp Ile Gly Tyr Glu His Thr Ser
65                  70                  75                  80

Phe Cys Gly Gln Gln Phe Ile Leu Glu Arg Gly Glu Tyr Pro Arg Trp
                85                  90                  95

Asp Ala Trp Ser Gly Ser Asn Ala Tyr His Met Glu Arg Leu Met Ser
            100                 105                 110

Phe Arg Pro Phe Cys Ser Ala Asn His Lys Glu Ser Lys Met Thr Ile
```

115                       120                          125
Phe Glu Lys Glu Asn Phe Ile Gly Arg Gln Trp Glu Ile Ser Asp Asp
    130                     135                 140

Tyr Pro Ser Leu Gln Ala Met Gly Trp Phe Asn Asn Glu Val Gly Ser
145                 150                 155                     160

Met Lys Ile Gln Ser Gly Ala Trp Val Cys Tyr His Tyr Leu Gly Tyr
                165                 170                 175

Arg Gly Tyr Gln Tyr Ile Leu Lys Cys Asp His His Glu Gly Asp Tyr
            180                 185                 190

Lys His Trp Arg Glu Trp Gly Ser His Ala Gln Thr Ser Gln Ile Gln
        195                 200                 205

Ser Ile Arg Arg Ile Gln Gln
210                 215

( 2 ) INFORMATION FOR SEQ ID NO: 2:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE:
                ( A ) DESCRIPTION: peptide ( x i ) SEQUENCE DESCRIPTION: SEQ ID NO: 2:

Ile Glu Thr Gln Ala Glu
 1               5   6

( 2 ) INFORMATION FOR SEQ ID NO: 3:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE:
                ( A ) DESCRIPTION: peptide ( x i ) SEQUENCE DESCRIPTION: SEQ ID NO: 3:

Met Ile Thr Gln Ala Glu
 1               5   6

( 2 ) INFORMATION FOR SEQ ID NO: 4:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE:
                ( A ) DESCRIPTION: peptide ( x i ) SEQUENCE DESCRIPTION: SEQ ID NO: 4:

Met Glu Ile Gln Ala Glu
 1               5   6

( 2 ) INFORMATION FOR SEQ ID NO: 5:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear (i i) MOLECULE TYPE:
(A) DESCRIPTION: peptide (x i) SEQUENCE DESCRIPTION: SEQ ID NO: 5:

Met Glu Thr Ile Ala Glu
 1            5    6

(2) INFORMATION FOR SEQ ID NO: 6:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE:
(A) DESCRIPTION: peptide (x i) SEQUENCE DESCRIPTION: SEQ ID NO: 6:

Met Glu Thr Gln Ile Glu
 1            5    6

(2) INFORMATION FOR SEQ ID NO: 7:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE:
(A) DESCRIPTION: peptide (x i) SEQUENCE DESCRIPTION: SEQ ID NO: 7:

Met Glu Thr Gln Ala Ile
 1            5    6

(2) INFORMATION FOR SEQ ID NO: 8:

(i) SEQUENCE CHARACTERISTICS:
(A) LENGTH: 205 amino acids
(B) TYPE: amino acid
(C) STRANDEDNESS: single
(D) TOPOLOGY: linear (i i) MOLECULE TYPE:
(A) DESCRIPTION: protein (x i) SEQUENCE DESCRIPTION: SEQ ID NO: 8:

| Met | Ala | Ser | Asp | His | Gln | Thr | Gln | Ala | Gly | Lys | Pro | Gln | Ser | Leu | Asn |
|---|---|---|---|---|---|---|---|---|---|---|---|---|---|---|---|
| 1 | | | | 5 | | | | | 10 | | | | | 15 | |

| Pro | Lys | Ile | Ile | Ile | Phe | Glu | Gln | Glu | Asn | Phe | Gln | Gly | His | Ser | His |
|---|---|---|---|---|---|---|---|---|---|---|---|---|---|---|---|
| | | | 20 | | | | | 25 | | | | | 30 | | |

| Glu | Leu | Asn | Gly | Pro | Cys | Pro | Asn | Leu | Lys | Glu | Thr | Gly | Val | Glu | Lys |
|---|---|---|---|---|---|---|---|---|---|---|---|---|---|---|---|
| | | | 35 | | | | | 40 | | | | | 45 | | |

| Ala | Gly | Ser | Val | Leu | Val | Gln | Ala | Gly | Pro | Trp | Val | Gly | Tyr | Glu | Gln |
|---|---|---|---|---|---|---|---|---|---|---|---|---|---|---|---|
| | 50 | | | | | 55 | | | | | 60 | | | | |

| Ala | Asn | Cys | Lys | Gly | Glu | Gln | Phe | Val | Phe | Glu | Lys | Gly | Glu | Tyr | Pro |
|---|---|---|---|---|---|---|---|---|---|---|---|---|---|---|---|
| 65 | | | | | 70 | | | | | 75 | | | | | 80 |

| Arg | Trp | Asp | Ser | Trp | Thr | Ser | Ser | Arg | Arg | Thr | Asp | Ser | Leu | Ser | Ser |
|---|---|---|---|---|---|---|---|---|---|---|---|---|---|---|---|
| | | | | 85 | | | | | 90 | | | | | 95 | |

| Leu | Arg | Pro | Ile | Lys | Val | Asp | Ser | Gln | Glu | His | Lys | Ile | Ile | Leu | Tyr |
|---|---|---|---|---|---|---|---|---|---|---|---|---|---|---|---|
| | | | 100 | | | | | 105 | | | | | 110 | | |

| Glu | Asn | Pro | Asn | Phe | Thr | Gly | Lys | Lys | Met | Glu | Ile | Ile | Asp | Asp | Asp |
|---|---|---|---|---|---|---|---|---|---|---|---|---|---|---|---|
| | | | 115 | | | | | 120 | | | | | 125 | | |

Val Pro Ser Phe His Ala His Gly Tyr Gln Glu Lys Val Ser Ser Val
130                 135                 140

Arg Val Gln Ser Gly Thr Trp Val Gly Tyr Gln Tyr Pro Gly Tyr Arg
145                 150                 155                 160

Gly Leu Gln Tyr Leu Leu Glu Lys Gly Asp Tyr Lys Asp Ser Ser Asp
                165                 170                 175

Phe Gly Ala Pro His Pro Gln Val Gln Ser Val Arg Arg Ile Arg Asp
                180                 185                 190

Met Gln Trp His Gln Arg Gly Ala Phe His Pro Ser Asn
                195                 200                 205

( 2 ) INFORMATION FOR SEQ ID NO: 9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 9:

Gly Leu Thr Glu Thr Gln Ala Glu Ala Ile Leu Glu
1               5                   10      12

( 2 ) INFORMATION FOR SEQ ID NO: 10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 10:

Met Gln Tyr His Tyr Leu Gly Arg Thr Gly Tyr Thr
1               5                   10      12

( 2 ) INFORMATION FOR SEQ ID NO: 11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 11:

Asp Phe Ala Thr Ile Phe Glu Lys Asn Ala Phe Leu
1               5                   10      12

( 2 ) INFORMATION FOR SEQ ID NO: 12:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 12:

```
Gln  Lys  Leu  Gly  Pro  Trp  Lys  Arg  Pro  Val  Ala  Tyr
 1              5                        10        12
```

(2) INFORMATION FOR SEQ ID NO: 13:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 13:

```
Met  Glu  Thr  Gln  Ala  Glu  Gln  Gln  Glu  Leu  Glu  Thr  Leu  Pro  Thr  Thr
 1              5                        10                       15
Lys  Met  Ala
          19
```

(2) INFORMATION FOR SEQ ID NO: 14:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 14:

```
Thr  Thr  Lys  Met  Ala  Gln  Thr  Asn  Pro  Thr  Pro  Gly  Ser  Leu  Gly  Pro
 1              5                        10                       15
Trp  Lys  Ile
          19
```

(2) INFORMATION FOR SEQ ID NO: 15:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 15:

```
Gly  Pro  Trp  Lys  Ile  Thr  Ile  Tyr  Asp  Gln  Glu  Asn  Phe  Gln  Gly  lys
 1              5                        10                       15
Arg  Met  Glu
          19
```

(2) INFORMATION FOR SEQ ID NO: 16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 16:

```
Gly  lys  Arg  Met  Glu  Phe  Thr  Ser  Ser  Cys  Pro  Asn  Val  Ser  Glu  Arg
 1              5                        10                       15
```

Ser Phe Asp
          19

(2) INFORMATION FOR SEQ ID NO: 17:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 17:

Glu Arg Ser Phe Asp Asn Val Arg Ser Leu Lys Val Glu Ser Gly Ala
 1               5                   10                  15
Trp Ile Gly
          19

(2) INFORMATION FOR SEQ ID NO: 18:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 18:

Gly Ala Trp Ile Gly Tyr Glu His Thr Ser Phe Cys Gly Gln Gln Phe
 1               5                   10                  15
Ile Leu Glu
          19

(2) INFORMATION FOR SEQ ID NO: 19:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 19:

Gln Phe Ile Leu Glu Arg Gly Glu Tyr Pro Arg Trp Asp Ala Trp Ser
 1               5                   10                  15
Gly Ser Asn
          19

(2) INFORMATION FOR SEQ ID NO: 20:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 20:

```
Trp  Ser  Gly  Ser  Asn  Ala  Tyr  His  Met  Glu  Arg  Leu  Met  Ser  Phe  Arg
 1              5                   10                       15

Pro  Phe  Cys
          19
```

( 2 ) INFORMATION FOR SEQ ID NO: 21:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 21:

```
Phe  Arg  Pro  Phe  Cys  Ser  Ala  Asn  His  Lys  Glu  Ser  Lys  Met  Thr  Ile
 1              5                   10                       15

Phe  Glu  Lys
          19
```

( 2 ) INFORMATION FOR SEQ ID NO: 22:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 22:

```
Thr  Ile  Phe  Glu  Lys  Glu  Asn  Phe  Ile  Gly  Arg  Gln  Trp  Glu  Ile  Ser
 1              5                   10                       15

Asp  Asp  Tyr
          19
```

( 2 ) INFORMATION FOR SEQ ID NO: 23:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 23:

```
Ile  Ser  Asp  Asp  Tyr  Pro  Ser  Leu  Gln  Ala  Met  Gly  Trp  Phe  Asn  Asn
 1              5                   10                       15

Glu  Val  Gly
          19
```

( 2 ) INFORMATION FOR SEQ ID NO: 24:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear (i i) MOLECULE TYPE:
  (A) DESCRIPTION: peptide (x i) SEQUENCE DESCRIPTION: SEQ ID NO: 24:

Asn Asn Glu Val Gly Ser Met Lys Ile Gln Ser Gly Ala Trp Val Cys
1               5                   10                  15
Tyr His Tyr
        19

(2) INFORMATION FOR SEQ ID NO: 25:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE:
    (A) DESCRIPTION: peptide (x i) SEQUENCE DESCRIPTION: SEQ ID NO: 25:

Val Cys Tyr His Tyr Leu Gly Tyr Arg Gly Tyr Gln Tyr Ile Leu Lys
1               5                   10                  15
Cys Asp His
        19

(2) INFORMATION FOR SEQ ID NO: 26:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE:
    (A) DESCRIPTION: peptide (x i) SEQUENCE DESCRIPTION: SEQ ID NO: 26:

Leu Lys Cys Asp His His Glu Gly Asp Tyr Lys His Trp Arg Glu Trp
1               5                   10                  15
Gly Ser His
        19

(2) INFORMATION FOR SEQ ID NO: 27:

(i) SEQUENCE CHARACTERISTICS:
    (A) LENGTH: 19 amino acids
    (B) TYPE: amino acid
    (C) STRANDEDNESS: single
    (D) TOPOLOGY: linear (i i) MOLECULE TYPE:
    (A) DESCRIPTION: peptide (x i) SEQUENCE DESCRIPTION: SEQ ID NO: 27:

Glu Trp Gly Ser His Ala Gln Thr Ser Gln Ile Gln Ser Ile Arg Arg
1               5                   10                  15
Ile Gln Gln
        19

(2) INFORMATION FOR SEQ ID NO: 28:

(i) SEQUENCE CHARACTERISTICS:
    (A) LENGTH: 6 amino acids
    (B) TYPE: amino acid (C) STRANDEDNESS: single
                (D) TOPOLOGY: linear (ii) MOLECULE TYPE:
                (A) DESCRIPTION: peptide (xi) SEQUENCE DESCRIPTION: SEQ ID NO: 28:

Met  Glu  Thr  Gln  Ala  Glu
 1              5    6

(2) INFORMATION FOR SEQ ID NO: 29:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE:
                (A) DESCRIPTION: peptide (xi) SEQUENCE DESCRIPTION: SEQ ID NO: 29:

Gln  Gln  Glu  Leu  Glu  Thr
 1              5    6

(2) INFORMATION FOR SEQ ID NO: 30:

(i) SEQUENCE CHARACTERISTICS:
                (A) LENGTH: 7 amino acids
                (B) TYPE: amino acid
                (C) STRANDEDNESS: single
                (D) TOPOLOGY: linear (ii) MOLECULE TYPE:
                (A) DESCRIPTION: peptide (xi) SEQUENCE DESCRIPTION: SEQ ID NO: 30:

Leu  Pro  Thr  Thr  Lys  Met  Ala
 1              5         7

(2) INFORMATION FOR SEQ ID NO: 31:

(i) SEQUENCE CHARACTERISTICS:
                (A) LENGTH: 17 amino acids
                (B) TYPE: amino acid
                (C) STRANDEDNESS: single
                (D) TOPOLOGY: linear (ii) MOLECULE TYPE:
                (A) DESCRIPTION: peptide (xi) SEQUENCE DESCRIPTION: SEQ ID NO: 31:

Met  Ala  Ser  Asp  His  Gln  Thr  Gln  Ala  Gly  Lys  Pro  Gln  Ser  Leu  Asn
 1              5                        10                       15
Pro
 17

(2) INFORMATION FOR SEQ ID NO: 32:

(i) SEQUENCE CHARACTERISTICS:
                (A) LENGTH: 17 amino acids
                (B) TYPE: amino acid
                (C) STRANDEDNESS: single
                (D) TOPOLOGY: linear (ii) MOLECULE TYPE:

( A ) DESCRIPTION: peptide ( x i ) SEQUENCE DESCRIPTION: SEQ ID NO: 32:

Gln Ser Leu Asn Pro Lys Ile Ile Ile Phe Glu Gln Glu Asn Phe Gln
1               5                   10                  15
Gly
17

( 2 ) INFORMATION FOR SEQ ID NO: 33:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 33:

Glu Asn Phe Gln Gly His Ser His Glu Leu Asn Gly Pro Cys Pro Asn
1               5                   10                  15
Leu
17

( 2 ) INFORMATION FOR SEQ ID NO: 34:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 34:

Pro Cys Pro Asn Leu Lys Glu Thr Gly Val Glu Lys Ala Gly Ser Val
1               5                   10                  15
Leu
17

( 2 ) INFORMATION FOR SEQ ID NO: 35:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 35:

Ala Gly Ser Val Leu Val Gln Ala Gly Pro Trp Val Gly Tyr Glu Gln
1               5                   10                  15
Ala
17

( 2 ) INFORMATION FOR SEQ ID NO: 36:

( i ) SEQUENCE CHARACTERISTICS:
        ( A ) LENGTH: 17 amino acids
        ( B ) TYPE: amino acid
        ( C ) STRANDEDNESS: single (D) TOPOLOGY: linear (ii) MOLECULE TYPE:
(A) DESCRIPTION: peptide (xi) SEQUENCE DESCRIPTION: SEQ ID NO: 36:

Gly Tyr Glu Gln Ala Asn Cys Lys Gly Glu Gln Phe Val Phe Glu Lys
1               5                   10                  15
Gly
17

(2) INFORMATION FOR SEQ ID NO: 37:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE:
(A) DESCRIPTION: peptide (xi) SEQUENCE DESCRIPTION: SEQ ID NO: 37:

Val Phe Glu Lys Gly Glu Tyr Pro Arg Trp Asp Ser Trp Thr Ser Ser
1               5                   10                  15
Arg
17

(2) INFORMATION FOR SEQ ID NO: 38:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE:
(A) DESCRIPTION: peptide (xi) SEQUENCE DESCRIPTION: SEQ ID NO: 38:

Trp Thr Ser Ser Arg Arg Thr Asp Ser Leu Ser Ser Leu Arg Pro Ile
1               5                   10                  15
Lys
17

(2) INFORMATION FOR SEQ ID NO: 39:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE:
(A) DESCRIPTION: peptide (xi) SEQUENCE DESCRIPTION: SEQ ID NO: 39:

Leu Arg Pro Ile Lys Val Asp Ser Gln Glu His Lys Ile Ile Leu Tyr
1               5                   10                  15
Glu
17

(2) INFORMATION FOR SEQ ID NO: 40:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE:
    ( A ) DESCRIPTION: peptide ( x i ) SEQUENCE DESCRIPTION: SEQ ID NO: 40:

```
Ile Ile Leu Tyr Glu Asn Pro Asn Phe Thr Gly Lys Lys Met Glu Ile
 1               5                   10                  15
Ile
 17
```

( 2 ) INFORMATION FOR SEQ ID NO: 41:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 41:

```
Lys Met Glu Ile Ile Asp Asp Asp Val Pro Ser Phe His Ala His Gly
 1               5                   10                  15
Tyr
 17
```

( 2 ) INFORMATION FOR SEQ ID NO: 42:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 42:

```
His Ala His Gly Tyr Gln Glu Lys Val Ser Ser Val Arg Val Gln Ser
 1               5                   10                  15
Gly
 17
```

( 2 ) INFORMATION FOR SEQ ID NO: 43:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( x i ) SEQUENCE DESCRIPTION: SEQ ID NO: 43:

```
Arg Val Gln Ser Gly Thr Trp Val Gly Tyr Gln Tyr Pro Gly Tyr Arg
 1               5                   10                  15
Gly
```

17

(2) INFORMATION FOR SEQ ID NO: 44:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 44:

Pro Gly Tyr Arg Gly Leu Gln Tyr Leu Leu Glu Lys Gly Asp Tyr Lys
 1            5                  10               15

Asp
17

(2) INFORMATION FOR SEQ ID NO: 45:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 45:

Gly Asp Tyr Lys Asp Ser Ser Asp Phe Gly Ala Pro His Pro Gln Val
 1            5                  10               15

Gln
17

(2) INFORMATION FOR SEQ ID NO: 46:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 46:

His Pro Gln Val Gln Ser Val Arg Arg Ile Arg Asp Met Gln Trp His
 1            5                  10               15

Gln
17

(2) INFORMATION FOR SEQ ID NO: 47:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE:
        (A) DESCRIPTION: peptide (xi) SEQUENCE DESCRIPTION: SEQ ID NO: 47:

-continued

| Arg | Ile | Arg | Asp | Met | Gln | Trp | His | Gln | Arg | Gly | Ala | Phe | His | Pro | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asn
17